United States Patent [19]

Stojkoski

[11] Patent Number: 5,017,367

[45] Date of Patent: May 21, 1991

[54] SKIN TREATMENT PREPARATION

[76] Inventor: Radmila G. Stojkoski, 35026 Lana La., Sterling Heights, Mich. 48077

[21] Appl. No.: 835

[22] Filed: Jan. 6, 1987

Related U.S. Application Data

[63] Continuation-in-part of Ser. No. 656,520, Oct. 1, 1984, abandoned, which is a continuation-in-part of Ser. No. 601,426, Apr. 18, 1984, abandoned.

[51] Int. Cl.$^5$ ................................................ A61K 7/21
[52] U.S. Cl. ...................................... 424/63; 424/604
[58] Field of Search .................................. 424/63, 131

[56] References Cited

U.S. PATENT DOCUMENTS 4,297,374 10/1981 Wess ...................................... 514/777
4,608,392 8/1986 Jacquet et al. ......................... 424/63

FOREIGN PATENT DOCUMENTS 2600388 7/1977 Fed. Rep. of Germany ...... 424/131

OTHER PUBLICATIONS

Ash et al., "A Formulary of Cosmetic Preparations", Chemical Pub. Co. (N.Y.) pp. 248–249, 397–398, 422 (1980).
Gregory, "Uses and Applications of Chemicals and Related Materials", Reinhold Pub. Corp. (N.Y.), p. 109 (1944).
Harry, "Cosmetic Materials, vol. II", Chemical Pub. Co. (N.Y.) pp. 457–458 (1963).
Pharmaceutical Formulas, vol. I, 12th Ed., The Chemist and Druggist Pub. (London) p. 650 (1953).
Pharmaceutical Formulas, vol. II, 10th Ed., The Chemist and Druggist Pub. (London) pp. 444–452, 555 (1946).
Puritan's Pride Pamphlet—"Honey Almond Deep Cleansing Facial Scrub"—p. 5 (1983).

*Primary Examiner*—Leonard Schenkman
*Attorney, Agent, or Firm*—Weintraub, DuRoss & Brady

[57] ABSTRACT

A skin treatment composition suitable for topical application containing:
  an organic carrier medium consisting of olive oil, butter and honey;
  an adsorptive agent, cornstarch, present in a ratio of about 0.25 to about 1 part adsorptive agent to about 1 part carrier medium;
  sodium acid pyrophosphate present in a ratio of between about 0.001 and about 0.1 part sodium acid pyrophosphate to about 1 part carrier medium; and
  distilled water present in a ratio of about 0.001 to about 1 part water to about 1 part medium.

3 Claims, No Drawings

SKIN TREATMENT PREPARATION

CROSS-REFERENCE TO RELATED APPLICATION

This application is a continuation-in-part of Ser. No. 656,520, filed Oct. 1, 1984, now abandoned, which is a continuation-in-part of application Ser. No. 601,426, filed Apr. 18, 1984 now abandoned.

BACKGROUND OF THE INVENTION

1. Field of the Invention:

This invention is related to topical applications for the cleaning and treatment of the skin. More specifically, this invention concerns a composition for the topical application to facial skin for cleansing, moisturizing and the promotion of the healing of minor skin irritations.

2. Brief Discussion of the Prior Art:

Various preparations have heretofore been proposed as topical skin care preparations. Among these are U.S. Pat. No. 4,297,374 to Wess which teaches the use of baking powder in admixture with orange juice, vegetable shortening and fresh produce such as bananas or avocados as a skin cleansing or moisturizing creme.

Additionally, a variety of preparations have heretofore been known which contain sodium bicarbonate as a thickener. Such preparations have been found to have limited effectiveness as cleansing agents. Specifically, skin care preparations heretofore produced containing sodium bicarbonate exhibit only minimal cleaning and moisturizing action and do not appear to promote healing of minor skin irritations.

Thus, it would be desirable to prepare a skin treatment composition which is gentle enough for topical application on delicate or sensitive skin such as those found on the face. It is also desirable that the topical skin composition be effective for cleaning delicate skin areas. It is also desirable that the topical skin composition be capable of removing dirt, sloughed-off skin cells and other detritus which adheres to the skin and accumulates in the pores. It is also desirable that the skin treatment composition be capable of moisturizing the skin areas and suitable for the promotion of healing of skin irritations such as minor rashes, transitory blemishes (i.e. blackheads, pimples) and the like.

SUMMARY OF THE INVENTION

This invention is predicated on the unexpected discovery that the incorporation of sodium acid pyrophosphate in certain topical skin treatment compositions provides increased cleansing, moisturizing and healing effects over conventional, known skin care and treatment compositions. It has also been found, quite unexpectedly, that sodium acid pyrophosphate has a bacteriocidal or bacteriostatic effect; reducing the number of bacteria which cause blackheads and other skin irritations present on the skin surface.

The skin treatment composition of the present invention consists essentially of:

(a) an organic carrier medium;

(b) a thickening agent present in a ratio between about 0.25 and about 1 part thickening agent per 1 part organic carrier medium;

(c) sodium acid pyrophosphate present in an amount between about 0.001 and about 0.1 parts pyrophosphate per 1 part carrier medium upon the total weight of the composition; and (d) water in a ratio between about 0.001 to about 1 part water per 1 part carrier.

The composition may also, optionally, contain various healing agents, preservatives, coloring agents and perfumes as desired.

DETAILED DESCRIPTION OF THE PREFERRED EMBODIMENT

In the skin treatment composition of the present invention, various thickeners and moisturizers are admixed with the active ingredient sodium acid pyrophosphate to produce a highly effective topical skin care composition which can be used as a cleaner, moisturizer and healing agent for minor skin irritations. The topical skin care composition of the present invention consists essentially of:

(a) an organic carrier base;

(b) an organic adsorption agent present in a ratio between about 0.25 and about 1 part thickening agent to about 1 part organic carrier;

(c) sodium acid pyrophosphate present in a ratio of between about 0.001 and about 0.1 part sodium and pyrophosphate to about 1 part organic carrier; and (d) water present in a ratio of between about 0.001 to about 1 part water per 1 part organic carrier in an emulsified state with the organic carrier base.

As can be readily appreciated, the topical skin care composition of the present invention can be formulated as a creme, salve, paste or the like. Parts by weight are based on a composition of about 225 parts. In the preferred embodiment, the proportions are adjusted such that the admixture of the above-listed ingredients forms a creme or salve. In such formulations, the organic carrier and water are adjusted such that the ratio of carrier to water is an amount ranging from about 5 to about 25 parts carrier per each part water.

The carrier is composed of butter and a liquid food-grade oil. In addition to the ability of these components to maintain water and the sodium acid pyrophosphate in a dispersed and emulsified state, these components act as a moisturizer when applied to the skin. In the preferred embodiment, the carrier is composed of butter, olive oil and honey. In the preferred embodiment, the carrier is between about 40 and about 75 percent by weight butter based on the total weight of the carrier and olive oil in an amount between about 24 percent by weight and about 55 percent by weight. Additionally, trace amounts of honey can be added to the carrier. In the preferred embodiment, honey is added in an amount between about 0.05 percent by weight and about 1 percent by weight based on the total weight of the carrier.

The skin treatment composition also contains an organic adsorptive agent. This material is generally a powdered granulated or particulate solid capable of thickening the carrier base. Ideally, the organic thickening agent employed in the present invention is capable of adsorbing or absorbing excess oils which may be present on the skin. Additionally, the particulate thickener present provides a "matte-like", natural appearance if the skin treatment composition is to be applied to the skin for prolonged periods. It has been found that a starch-based agent is most advantageously employed herein. In the preferred embodiment, commercially-available food-grade cornstarch is selected.

Sodium acid pyrophosphate employed in the present invention is, preferably, admixed into the carrier medium as a granulated or powdered solid material. The amount of sodium acid pyrophosphate present in the skin treatment composition of the present invention is in a ratio of between about 0.001 parts and about 0.1 parts sodium acid pyrophosphate per 1 part carrier.

Sodium acid pyrophosphate is commercially available from numerous chemical supply houses. Another suitable source of sodium acid pyrophosphate is found in a type of baking powder manufactured in West Germany and Canada under the trade name OETKER. This baking powder contains leavening agents consisting essentially of a mixture of sodium bicarbonate and sodium acid pyrophosphate in proportions of approximately two parts sodium acid pyrophosphate to one part sodium bicarbonate. The presence of sodium bicarbonate in the mixture when OETKER baking powder is employed as the sodium acid pyrophosphate source in no way impairs the performance of the skin treatment composition of the present invention.

The presence of sodium acid pyrophosphate in the composition of the present invention markedly reduces the number of blemishes attributable to bacteria present on the skin and in pores. Without being bound to any theory, it is believed that sodium acid pyrophosphate acts as a bacteriocidal or bacteriostatic agent; killing or inactivating various microorganisms present on the skin surface. The sodium acid pyrophosphate appears to have an astringent effect without the harshness of conventional astringents.

The topical skin care composition of the present invention can also contain optional ingredients such as perfumes, coloring agents and the like. The perfumes preferred can be selected from any suitable commercially available fragrance. The coloring agent, where used, is employed to leave a pleasing skin tone when the topical skin care composition is applied. On such coloring agent is cocoa powder present in the skin care composition in a ratio between about 0.001 and about 1.0 part cocoa powder per 1 part carrier base.

It is also within the purview of this invention to incorporate various other optional compounds in the skin treatment composition of the present invention. It has been found that bismuth subnitrate, when employed in a ratio of between about 0.001 and about 0.1 part bismuth subnitrate to 1 part carrier base exhibits therapeutic properties as a healing agent for minor epidermal skin irritations.

The topical skin care composition of the present invention can also, optionally, contain a variety of suitable preservatives. It has been found that a compound selected from the group consisting of salicylic acid, alkali metal salicylates and mixtures therof exhibits preservative qualities when employed in the skin treatment composition. When employed in the present invention, the preservative is present in a ratio between about 0.001 and about 0.1 part preservative to about 1 part carrier base. It has also been found, quite unexpectedly, that salicylic acid or the salicylate salts thereof are effective to forestall and minimize wrinkles when employed in the skin treatment composition of the present invention in the amounts listed above.

In preparing the present composition, the components of the carrier, water, sodium acid pyrophosphate, adsorbent, and any optional ingredients are admixed in a given order at standard temperature and pressure. First, the organic components of the carrier are thoroughly blended. Water is added to the blended organic components and mixed at high speed to create an organic-aqueous emulsion. Mixing proceeds for approximately 15 minutes. It is to be understood that the consistency of the emulsion will vary given the mixing speed and mixing time employed. However, extremely fine emulsions having highly dispersed water are preferred. After the emulsion is formed, the sodium acid pyrophosphate, cornstarch, and any optional ingredients are added thereto. This admixture is then mixed to provide a homogenous mixture of appropriate consistency. It is to be understood that variances in the ratio of water and dry ingredients to carrier base will yield skin treatment compositions of different consistencies varying from lotion to ointment to cream to paste as desired.

Where the additional ingredients are employed, the skin treatment composition of the present invention is prepared by blending the healing agents such as bismuth subnitrate, the preservatives such as salicylic acid and the coloring agents into the composition together with the sodium acid pyrophosphate. It should be noted that the optional ingredients need not all be utilized at one time. Rather, any optional ingredient, alone, or any combination thereof, can be used.

Without being bound to any theory, it is believed that the presence of sodium acid pyrophosphate in the skin treatment composition imparts unique astringent and cleansing properties to the skin treatment composition of the present invention. It is believed that the presence of sodium acid pyrophosphate acts in concert with the other compounds in the composition of the present invention to promote the dislodgement and removal of dirt, unwanted old makeup and dead epidermal cells from both the surface of the skin and within clogged pores without damaging existing healthy skin tissue. The astringent properties of the sodium acid pyrophosphate when employed in admixture with the components of the skin care composition of the present invention further assist in thorough skin cleansing. Those properties combined with the moisturizing properties of the present invention permit the skin treatment composition to provide thorough skin cleansing and moisturizing as well as preventing reoccurrence of such skin problems as blackheads for a substantial period after use.

The skin treatment composition of the present invention can be employed as a skin cleansing composition, a moisturizer-treatment masque or a concealing composition or a night cream depending on the formulation consistency.

When employed as a skin cleansing composition, the material generally has the consistency of a creme or a paste. The skin cleaning cream is massaged on the skin to be cleaned for a period of greater than 10 seconds and is then rinsed off with clean water. Excess water is gently dried from the skin.

When employed as a masque, the material has the consistency of a cream or paste and is gently spread over the skin and allowed to remain undisturbed for a period of between 30 seconds and about 15 minutes; after which time it can be gently removed and the face rinsed.

When employed as a night cream, the composition of the present invention, preferably, has the consistency of a lotion or salve. The night cream of the present invention is gently massaged into the skin before bed, any residue can be wiped gently off the face.

When employed as a concealing cream, the material will, generally, have the consistency of a salve and will have suitable pigments employed therein to approximate the skin tone of the user.

For a more complete understanding of the present invention, reference is made to the following examples. The following examples are illustrative of the present invention and are not intended in any way as a limitation upon the scope thereof. In the examples, all parts are by weight, absent any indications to the contrary.

EXAMPLE I

A topical skin treatment composition was prepared

A topical skin treatment composition was prepared by emulsifying one pound of butter, 1 cup olive oil and 2 spoons honey with ¾ cup of water at room temperature. To this mixture was added 3 teaspoons of salicylic acid, 3 teaspoons of Oetker baking powder and 1¾ cup cornstarch. The material was thoroughly mixed and resulted in a composition having a creamy consistency. The resulting composition was evaluated for its effect on skin.

The condition of the initial subject's skin was evaluated prior to beginning treatment. An area of dermatitis was noted which the subject reported as being itchy and inflamed. Several pronounced blackheads were also noted on the face. Areas of pronounced dry skin were found; particularly in the cheekbone region; indicated by overly taut skin and random flaking. Several minor wrinkles were also noted; particularly around the eyes.

The subject followed the following procedure for 30 days. The skin condition was monitored daily to detect changes. The face and neck areas were washed thoroughly with comfortably warm water. A liberal amount of the topical skin care composition was massaged into the washed skin. The face and neck were, then, patted with a very soft fabric pad to remove shininess from the skin. The subject then applied conventional makeup as desired. The cleansing and cream application were repeated twice daily; in the morning and before bed.

The subject reported a reduction in itching and irritation of the areas affected with dermatitis after using the cream for one day. Visual inspection of the affected areas indicated a reduction in redness at that time.

Daily inspection was continued. Redness and itching continued to be reduced with subsequent treatment. After seven days, the dryness was significantly reduced. The amount of dry skin and flaking was reduced and the overly taut or stretched skin areas were reduced. Additionally, the skin felt smoother when touched.

By the tenth day of treatment, there was a noticeable reduction in the number and size of blackheads. After 15 days, marked reduction in wrinkles around the eyes was noted.

Having thus described the invention, what is claimed is:

1. A skin treatment composition suitable for topical application consisting of an effective skin cleansing, moisturizing and healing amount of a composition consisting of:
    an organic carrier medium consisting of (a) olive oil, the olive oil being present in an amount of between 0.24 to about 0.55 parts per 1 part carrier medium;
    (b) butter present in an amount between 0.40 to 0.75 parts per 1 part carrier medium; and (c) honey present in an amount between 0.005 to 0.01 parts per 1 part carrier medium;
    an organic thickening and adsorptive agent consisting of cornstarch present in a ratio of about 0.25 to about 1 part adsorptive agent to about 1 part carrier medium;
    sodium acid pyrophosphate present in a ratio of between about 0.001 to about 0.1 part sodium acid pyrophosphate to about 1 part carrier medium;
    a preservative selected from the group consisting of: salicylic acid, alkali metal salicylates and mixtures thereof present in a ratio of between about 0.001 and 0.1 part preservative per one part carrier medium;
    bismuth subnitrate present in a ratio between about 0.001 and about 0.1 part bismuth subnitrate to about 1 part carrier medium;
    a coloring agent consisting of cocoa powder present in a ratio of between 0.001 and about 1.0 parts to 1 part carrier medium; and
    distilled water present in a ratio of about 0.001 to about 1 part water to about 1 part carrier medium.

2. The skin treatment composition of claim 1 wherein the carrier medium consists of butter, in an amount between about 40 and about 75 percent by weight based on the total weight of the carrier; olive oil present in an amount between about 26 and about 55 percent by weight, based on the total weight of the carrier, and honey present in an amount between 0.05 and about 1 percent by weight based on the total weight of the carrier.

3. A skin treatment composition suitable for topical application consisting of an effective skin cleansing moisturizing and healing amount of a composition consisting of:
    an organic carrier medium, the organic carrier medium being an aqueous-organic emulsion consisting of butter, olive oil and water, the water present in an amount approximately equal to the oil and butter;
    an organic thickening and adsorptive agent consisting of cornstarch present in a ratio of about 0.25 to about 1 part adsorptive agent to about 1 part carrier medium; and
    sodium acid pyrophosphate present in a ratio of between about 0.001 to about 0.1 part sodium acid pyrophosphate to about 1 part carrier medium;
    a preservative consisting of: salicylic acid, alkali metal silicylates and mixtures thereof present in a ratio of between 0.001 and 0.1 part preservative per 1 part carrier medium;
    bismuth subnitrate present in a ratio between about 0.001 and about 0.1 part bismuth subnitrate to about 1 part carrier medium;
    a coloring agent consisting of cocoa powder present in a ratio of between 0.001 and about 1.0 parts to 1 part carrier medium.

* * * * *